United States Patent
Barak

(10) Patent No.: US 9,935,362 B2
(45) Date of Patent: Apr. 3, 2018

(54) SYSTEMS, APPARATUSES AND METHODS FOR BIOMETRIC SENSING USING CONFORMAL FLEXIBLE ANTENNA

(71) Applicant: SENSIFREE LTD., Kfar Saba (IL)

(72) Inventor: Ilan Barak, Kfar Saba (IL)

(73) Assignee: SENSIFREE LTD., Kfar Saba (IL)

( * ) Notice: Subject to any disclaimer, the term of this patent is extended or adjusted under 35 U.S.C. 154(b) by 0 days.

(21) Appl. No.: 14/893,039

(22) PCT Filed: Nov. 18, 2015

(86) PCT No.: PCT/IB2015/058927
§ 371 (c)(1),
(2) Date: Mar. 29, 2017

(87) PCT Pub. No.: WO2016/083951
PCT Pub. Date: Jun. 2, 2016

(65) Prior Publication Data
US 2017/0229763 A1    Aug. 10, 2017

Related U.S. Application Data

(60) Provisional application No. 62/083,981, filed on Nov. 25, 2014.

(51) Int. Cl.
*H01Q 1/38* (2006.01)
*H01Q 1/27* (2006.01)
(Continued)

(52) U.S. Cl.
CPC .......... *H01Q 1/273* (2013.01); *A61B 5/02444* (2013.01); *A61B 5/0507* (2013.01);
(Continued)

(58) Field of Classification Search
CPC ........ H01Q 1/273; H01Q 13/106; H01Q 1/38; H01Q 5/25
See application file for complete search history.

(56) References Cited

U.S. PATENT DOCUMENTS 6,888,502 B2   5/2005   Beigel et al.
7,272,431 B2   9/2007   McGrath
2006/0066495 A1   3/2006   Isoifovich et al.

FOREIGN PATENT DOCUMENTS

JP    2009065321 A    3/2009

OTHER PUBLICATIONS

"International Search Report", dated Feb. 11, 2016, 3, ISA/USPTO, Alexandria, United States of America.
(Continued)

*Primary Examiner* — Andrea Lindgren Baltzell
(74) *Attorney, Agent, or Firm* — Neifeld IP Law, PC

(57) ABSTRACT

This invention provides conformal antenna structures, how to make and use the antenna structures, and systems in which the antenna structures may be used for biometric sensing of humans and other animals. The antenna structures of the invention includes at least one relatively flexible section connecting relatively rigid sections. The relatively flexible section connecting relatively rigid sections may flex so that the relatively rigid sections connected to the relatively flexible section can change orientation relative to one another. This allows the relatively rigid sections to be conformed to a region of a surface of a human or animal that is not flat (that is curved).

19 Claims, 5 Drawing Sheets

(51) Int. Cl.
*H01Q 13/10* (2006.01)
*A61B 5/05* (2006.01)
*H01Q 5/25* (2015.01)
*A61B 5/00* (2006.01)
*A61B 5/024* (2006.01)

(52) U.S. Cl.
CPC ............. *A61B 5/6824* (2013.01); *H01Q 1/38* (2013.01); *H01Q 5/25* (2015.01); *H01Q 13/106* (2013.01); *A61B 5/02438* (2013.01); *A61B 2562/164* (2013.01); *A61B 2562/166* (2013.01)

(56) References Cited

OTHER PUBLICATIONS

"Written Opinion of the International Search Authority", dated Feb. 11, 2016, 7, ISA/USPTO, Alexandria, United States of America.
"International Preliminary Report on Patentability Chapter I", dated May 30, 2017, 1, ISA/USPTO, Alexandria, United States of America.

SYSTEMS, APPARATUSES AND METHODS FOR BIOMETRIC SENSING USING CONFORMAL FLEXIBLE ANTENNA

BACKGROUND OF THE INVENTION

This invention relates to biometric sensing of human beings and other animals using wearable devices. We disclose herein a type of antenna useful, for example in the invention disclosed in WO213118121 titled "A microwave contactless heart rate sensor." The entire contents of WO/2013/118121 and U.S. provisional application 62/083, 981, filed Nov. 25, 2014 titled "Systems, Apparatuses and Methods for Biometric Sensing Using Conformal Flexible Antenna", are incorporated herein by reference.

It has been shown previously that radar technology may be used to estimate heart rates of humans or animals. For example, WIPO Patent Application WO/2013/118121, titled "A Microwave Contactless Heart Rate Sensor," filed on Feb. 7, 2013, and the entire contents of which is incorporated by reference herein, discloses an antenna that radiates radio frequency (RF) fields into tissues.

U.S. Pat. No. 3,031,665 describes a broadband magnetic antenna incorporating a ground plane directing the radiated energy only in one direction. The antenna disclosed in U.S. Pat. No. 3,031,665 is an rigid slot type antenna that has two parallel slots with an additional spacer slot.

The antenna for UWB (Ultra Wide Band) communication described in "A Microstrip-Fed Ultra-Wideband Slot Antenna", Antennas and Propagation Society International Symposium, APSURSI '09, IEEE, 2009, is bidirectional and rigid.

SUMMARY OF THE INVENTION

This invention provides conformal antenna structures, how to make and use the antenna structures, and systems in which the antenna structures may be used for biometric sensing of humans and other animals.

The antenna structures of the invention includes at least one relatively flexible section connecting relatively rigid sections. The relatively flexible section connecting relatively rigid sections may flex so that the relatively rigid sections connected to the relatively flexible section can change orientation relative to one another. This allows the relatively rigid sections to be conformed to a region of a surface of a human or animal that is not flat (that is curved).

Preferably, the antenna structures of the invention also include a ground plane. The existence of the ground plane limits radiation transmitted other than in the desired direction into the body of the human or animal. Alternatively, or in addition to a ground plane, the antenna structure may include a microwave absorber. The absorber absorbs radiation in other than the desired direction into the body of the human or animal.

The present disclosure provides systems, apparatuses and methods for biometrically sensing physiological parameters using radar technology. A thin miniaturized ultra wideband antenna that comprises a combination of relatively flexible and relatively rigid sections, is conformable to a curved portion of a surface of a body organ, and is useful for sensing biometric data. Examples of frequency ranges that may be used for sensing are from about 3.1 to about 10.6 GHz. The antenna structure may be constructed using relatively rigid printed circuit board (PCB) segments interconnected by relatively flexible portions to achieve conformability, broadband capability, low cost and unidirectional radiation characteristics. The relatively flexible sections are sufficiently flexible so that, for example, when worn as part of a wearable element, the relatively flexible sections will flex so that the antenna structure conforms to the surface of the body. The relatively flexible sections may for example be formed from a polyimide. Alternative relatively flexible materials include other flexible polymers, and composites comprising a polymer and other materials such as glass fabric. Any flexible material that is compatible with PCB manufacturing processes may be used for the flexible sections. These materials must be able to be metallized and to withstand temperatures of at least 160 Centigrade without irreversibly changing its dielectric constant, electrical conductivity, or relative flexibility by more than 10 percent. The relatively rigid section must be rigid enough to maintain the spatial separation of opposing metal surfaces.

The segments may be printed using a multilayer rigid PCB technology, where the interconnecting sections are realized on flexible section, allowing the antenna to conform to the limb to which it is attached. The antenna may be attached to the limb using a strap, for example, a wrist band of watch strap, so as to illuminate arteries beneath it (e.g., radial or ulnar artery at the wrist). However, such attachments may be imprecise in locating the antenna in the vicinity of the arteries, and for adequate operation, the width of the electromagnetic field generated by the antenna, also called the beam width, may be large enough to compensate for misplacement of the antenna. In some instances, the antenna may be isolated from the wrist tissue by using thermoplastic polyurethane (TPU), which is biocompatible, possesses good dielectric properties and has the flexibility needed for comfortable attachment to the human skin. In some instances, the PCB may include a ground plane on the back side to create a unidirectional radiation pattern.

Preferably, an antenna structure comprises a sequence of layers including: a first metal layer, a first dielectric layer which is relatively rigid, a second metallic layer, a second dielectric layer which is relatively flexible, and a third metal layer. Each layer may have a different spatial extent as another layer, which results in the antenna structure shown for example in FIG. 3.

Additional dielectric and metal layers may reside between the specified sequence of layers. For example, the first dielectric layer may be replaced by a first and another dielectric layers in contact with one another, or separated from one another at some locations by an additional metal layer. Moreover, additional layers may include relatively thin adhesive layers to adhere various layers to one another. Preferably, nonconductive adhesive or other nonconductive layers cover surfaces of metal layers.

The first metal layer defines a metallic conductive ground plane. Preferably, the first metallic layer is formed from copper. Preferably, this layer is from greater than one micron and 2000 microns, more preferably between 4 and 100 microns. Typically, copper on PC boards are 17-68 microns thick. Preferably, this layer has a conductivity of greater than 10,000,000 Siemens per meter.

The first dielectric layer provides spacing between metal layers. Preferably, the first dielectric layer is formed from a material having a dielectric constant between 1 and 200, more preferably between 2 and 11; and having a dielectric loss factor of less than 0.1 and more preferably less than 0.05 for all frequencies between 3.1 and 10.6 Ghz. Preferably, the first dielectric layer is formed from the same material used to form PC boards. Preferably, this material is an epoxy glass. This first dielectric material is part of the relatively rigid sections and not part of the relatively flexible sections.

The currently preferred material identified as FR4, which is a composite material composed of woven fiberglass cloth with an epoxy resin binder.

The second metal layer provides the antenna feed. Preferably, the second metal layer is formed from a material having the same preferred properties and thicknesses as the first metal layer, but preferably no thicker than 100 microns. The preferred material forming the second metal layer is copper. However, the first and second metal layers may be different metals. However, the second layer is not essential for providing the antenna feed. Instead, the antenna feed may be provided for example by a coaxial connection, or a microstrip line including metal above the third metal layer or below the first metal layer.

The second dielectric layer is sufficiently flexible so that it may flex to allow the relatively rigid sections (those sections including the relatively rigid first dielectric layer) to conform to a non flat surface. Preferably, the second dielectric layer is formed from material having a dielectric layer between 2 and 6; preferably the second dielectric layer is formed from material having a loss factor less than 0.02. Preferably, the second dielectric layer is formed a polymer or a composite material including a polymer. These polymers include polyester; polyimide; polyamide; and aramid. The second dielectric may be a composite of one or more polymers with a glass or other ceramic. Preferably, the relatively flexible second dielectric layer extends over the entire footprint of the antenna structure, which includes both the relatively rigid sections and the relatively flexible sections.

The third metal layer defines an aperture there through. Preferably, the third metal layer is formed from a material having the same preferred properties and thicknesses as the first metal layer, but preferably no thicker than 100 microns. Preferably, the third layer is formed from copper.

The antenna structure is fabricated so that it results in the relatively rigid sections connected by the relatively flexible sections. The relatively rigid sections each comprise a portion of the first metal layer (ground plane); a portion of the relatively rigid first dielectric layer; and a portion of the relatively flexible layer. Various regions of each relatively rigid section also include a portion of the third metallic layer. At least one of the relatively rigid sections also includes a portion, or all, of the second metallic layer providing the antenna feed.

The antenna structure is fabricated so that it results in the relatively flexible sections including a portion of the relatively flexible second dielectric layer. Preferably, the relatively flexible section also includes at least part of the second metal layer providing the antenna feed.

Preferably, the shape of each relatively rigid section is rectangular for ease of manufacturing. However, any shape is contemplated.

Preferably, the shape of each relatively flexible section is also rectangular.

Preferably, the antenna structure defines pathways through the first and second dielectric layers which contain conductive material. This conductive material in each pathway preferably contacts both the first metal layer and the third metal layer. Preferably, these conductive paths are define vias extending linearly to both the first metal layer and the third metal layer.

Preferably, these conductive paths are each located near the periphery of the of second dielectric layer. Preferably, the vias are spaced from one another between 0.1 and 5 millimeters, and more preferably 0.2-1.0 millimeters. Less preferably, the antenna structure includes side plating which provides a conductive layer on at least those side surfaces of the relatively rigid sections that define outer peripheral sides faces of the antenna structure. Preferably, these vias define a ring surrounding an aperture in the third metal layer as shown in FIG. 3. More preferably, the vias' ring is offset from the first and third metal edge by an essentially pre-defined distance, so as to form an open ended transmission line intended to suppress unwanted current on the first metal outer surface.

The antenna feed preferably connects to or is part of a conductive path that is conductively connected to an electronic circuit external to the antenna structure. This conductive path may include a via extending through either the first or second dielectric layer or a path extending to a peripheral side of the antenna structure.

Moreover, antenna structure may also comprise microwave absorbing material. For example, a thin, flexible, magnetically loaded, high-loss silicone rubber material for 6-35 GHz that is electrically non-conductive. This type of material is discussed in U.S. Pat. No. 5,275,880. Various microwave absorbing materials are commercially available. For example the materials under the trade name "Eccosorb" registered as U.S. trademark number 0643877, are microwave absorbing materials. The particularly preferred material contemplated by the inventor is trademark "Eccosorb GDS". These materials are commercially available. A paper describing properties of such a material comprising magnetic granular composites is Gama, "Complex permeability and permittivity variation of carbonyl iron rubber in the frequency range of 2 to 18 GHz", Journal of Aerospace Technology and Management," V. 2, n. 1, January-April 2010.

This microwave absorbing material may cover the side regions of the structure, such as the PCB side regions, between the ground plane structure and the antenna structure; also on the back side of the ground plate structure; and also in the bendable region or regions between rigid pieces of the dielectric, such as dielectric PC board, on which the antenna resides. This material may act to minimize radiation to free space from the antenna structure.

DETAILED DESCRIPTION OF THE EMBODIMENTS

Embodiments of antenna structure implementations conformable to a cylindrical body organ for sensing biometric data are disclosed herein. The disclosed methods, apparatuses and systems discuss embodiments of an ultra wideband miniaturized thin antenna implementation that is conformable to a curved portion of a body limb for sensing biometric data. In some instances, the antenna may be constructed using rigid flex PCB technology to achieve conformability, broadband capability, low cost and unidirectional radiation characteristics.

Examples of body organs to which the antenna structure implementations can conform include cylindrical surface regions of a body organ. These regions include wrist, arm, neck, head, leg, ankle, shoulder, and chest.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., at least one of functionally and structurally similar).

FIG. 1 does not show a means to feed, in other words, excite, the antenna structure.

DETAILED DESCRIPTION OF SOME OF THE EMBODIMENTS

Figure 1:
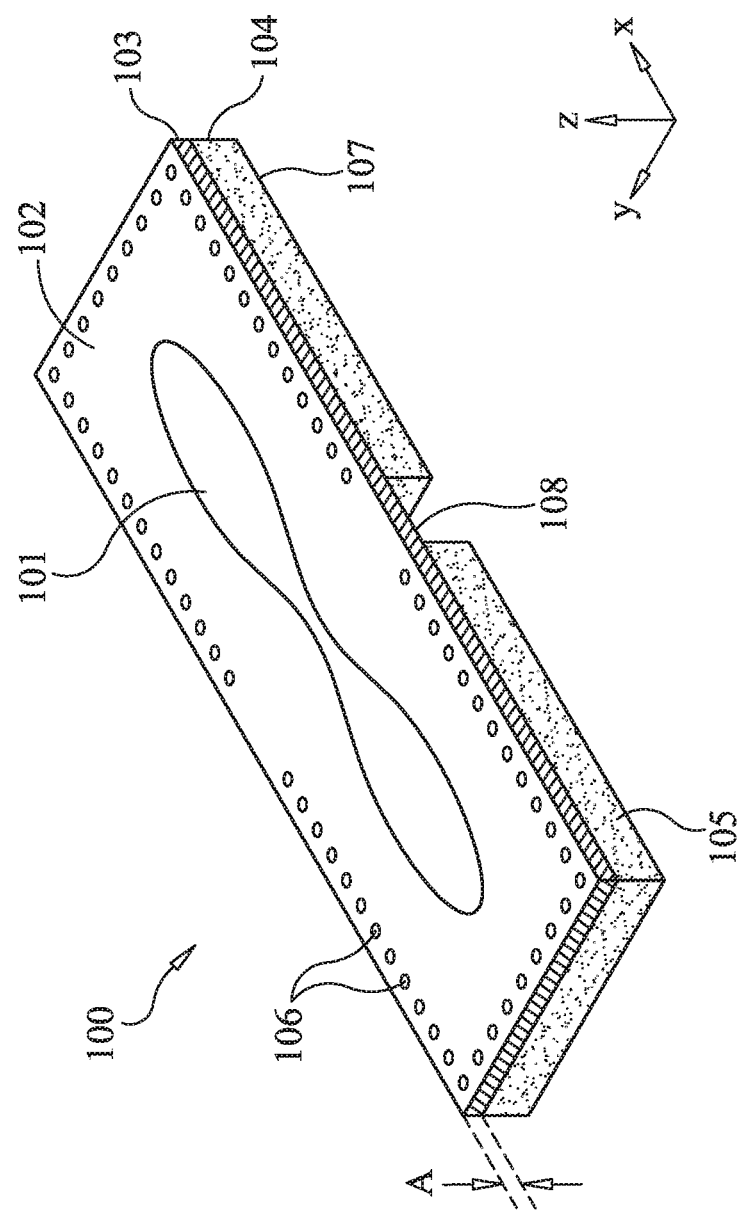
FIG. 1 is a perspective view of an example embodiment of an ultra wideband microwave signal antenna structure used for sensing, for example, arteries, and an x-y-z coordinate system for orientation.

FIG. 1 shows ultra wideband microwave signal antenna structure 100 comprising opening or slot 101; metal plane 102; flexible PCB part 103; first rigid PCB section 104; second rigid PCB section 105; row or ring of vias 106; ground plane on the back side 107; and flexible section 108.

FIG. 1 shows an antenna structure 100 comprising a metal plane 102 with an opening or slot 101. First rigid PCB section 104 and second rigid PCB section 105 may be covered and adhered to a flexible PCB part 103 comprising a flexible section 108 that may serve as an interconnecting portion for the first and second PCB sections, allowing the antenna to conform to a limb to which it may be attached. Rigid PCB sections 104, 105, are an embodiments of the relatively rigid sections discussed above. Flexible PCB part 103 is an embodiment of the relatively flexible section discussed above. The slot may be designed in a variety of shapes to achieve desired characteristics, including a taper design that gradually increases the slot characteristic impedance from twice the terminal impedance (e.g., slot characteristic impedance of about 100 ohm for a 50 ohm terminal impedance) to as high as practical before the slot gets terminated. For example, the slot may be shaped so that the antenna is well matched in a bandwidth of at least 5 GHz in a UWB of 3.1 GHz to 10.6 GHz. In some instances, a longer slot length may lead to a lower center frequency, and a larger taper end width before the circular termination results in a wider antenna bandwidth. For example, the design of the slot width may follow the following configuration: for $|x|<x_0$, the slot width $s(x)$ may be designed following the equation $s(x)=2 S_0 e^{k|x|}$, while for $|x|\geq x_0$, it may be designed so that $s(x)$ may have a shape of a circle centered around $x=x_0+k\ s^2\ (x_0)$ with radius R=the square root of $\{s^2(x_0)+k\ s^2(x_0)\}$.

For $X<-X0, x=-X0-kS^2(X0)$

These substantially circle shape terminated exponential taper slot shapes may be useful for attaining at least one of ultra wide broadband and large beam-width. In some instances, the antenna performance may not be sensitive to the exact shape of the slot, and deviations in the width of the slot (e.g., a few tens percent) may have limited effect on the antenna performance. In some instances, the shape of the antenna may be designed so as to account for some variations in the placement of the antenna proximate to a limb. For example, the slot may be shaped so as to allow for heart rate detection when positioned above an artery in the wrist area, even if the antenna is misplaced by up to 6 mm. In some instances, the PCB antenna structure may include a ground plane on the back side 107, creating a unidirectional radiation pattern. This backplane may be connected to the top metal surrounding the slot by a row (or ring) of vias 106, traversing the thickness of the antenna, and providing the equivalent electrical function of a continuous metal wall.

The antenna structure 100 may be included as part of a wearable device (not shown). The wearable device may embed the antenna structure in a strap or clothing element, and may include polymer layers bonded to the antenna structure 100.

Figure 2:
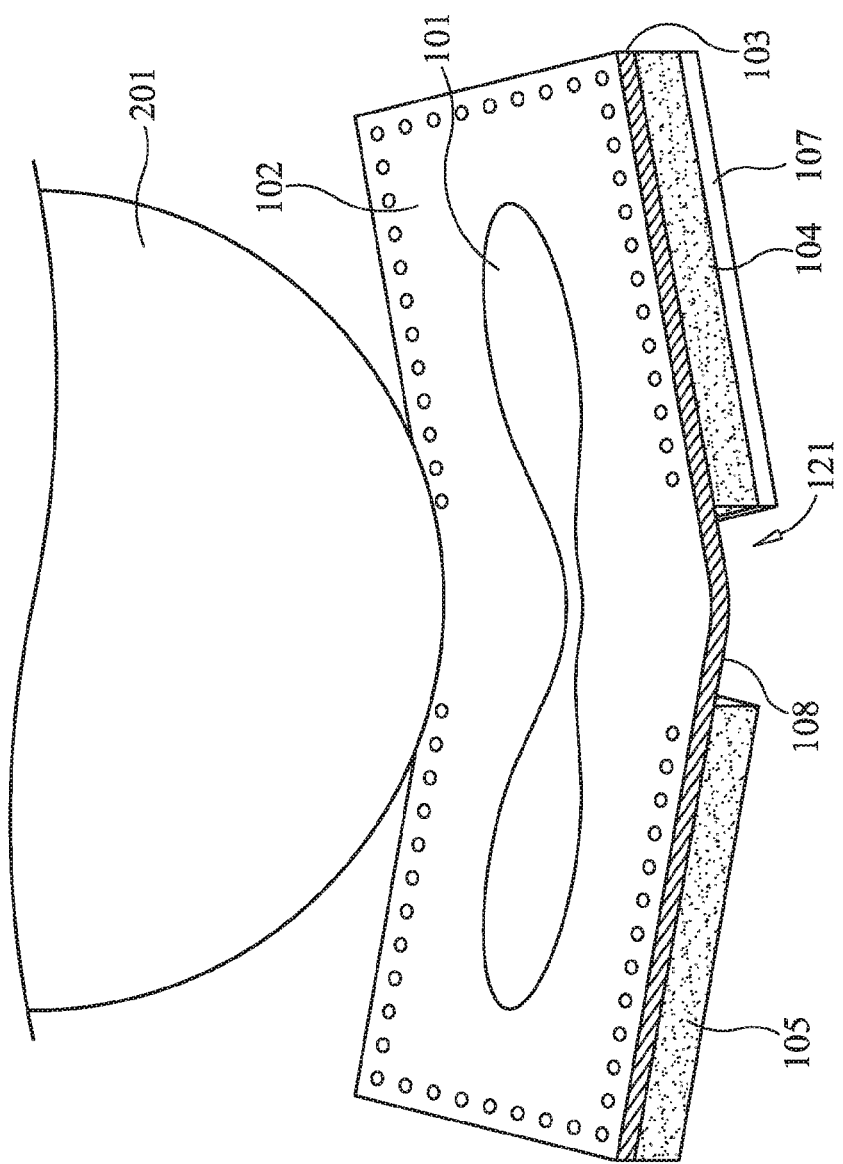
FIG. 2 perspective view of an example of positioning of the antenna structure with respect to a limb containing an artery to be sensed.

FIG. 2 shows limb 201 and antenna structure 100. The antenna structure 100 is positioned with respect to a limb 201 containing an artery to be sensed. FIG. 2 shows rigid section 104 canted at an angle relative to rigid section 105 due to a bend (also called flex) in relatively flexible section 108. Preferably, the first rigid PCB section 104 and the second rigid PCB section 105 may be separated by a groove 121 to facilitate flexibility of the interconnecting flexible section 108 of the PCB part 103 so as to allow the antenna to conform to the shape of the limb. However, the groove (that is spatial extent along the direction of the text in FIG. 2) is not essential to flexing of the flexible section. All that is required is the flexible section can act as a hinge in at least one dimension. The relatively flexible section 108 may not be shielded by a backplane to not interfere with the flexibility. It is difficult to economically manufacture a zero length flexible hinge using conventional PCB manufacturing technology. However, the flexible section should be made as short as feasible for various reasons.

Figure 5:
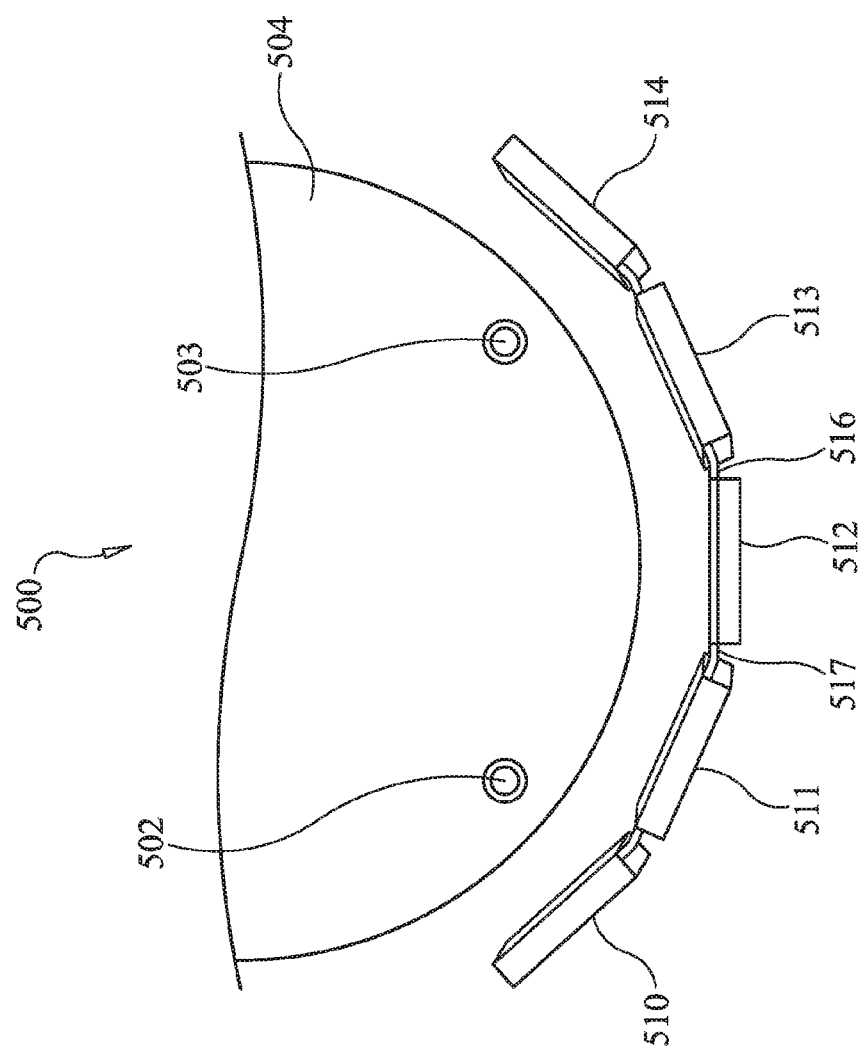
FIG. 5 is a mixed sectional and perspective view of a body part, and a compound antenna structure comprising two antenna structures, a separating section, and relatively flexible sections.

FIG. 5 illustrates a a compound antenna structure and positioning of the compound antenna structure near two arteries of a body part. FIG. 500 shows compound antenna structure 500 comprising relatively rigid antenna sections 510, 511, 513, and 514; and also 512. Relatively rigid sections 510 and 511 and an intervening relatively flexible section (unnumbered) define one antenna structure. Relatively rigid sections 513 and 514 and an intervening relatively flexible section (unnumbered) define another antenna structure. Each antenna structure is spaced apart from the other by relatively rigid section 512, and relatively flexible sections 516 and 517. Relatively flexible sections 516, 517 also connect the relatively rigid section 512 to the two antennas. The antenna structure comprising the two antenna halfs 510, 511 are positioned relatively close to radial or ulnar artery 502. The antenna structure comprising the other two antenna halfs 513, 514 are positioned relatively close to the other one of the radial or ulnar artery 503. The sections 510, 511, 513, and 514; and also 512 comprise PCB. PCB part 512 may also serve as connection points for sensor electronics.

As shown, each antenna structure is positioned relatively close to a respective artery in the body part for sensing changes in that artery.

Each pair or relatively rigid sections is connected by a relatively flexible section. Hence, in some embodiments, only one pair relatively rigid sections connected by a single relatively flexible section exist.

Figure 3:
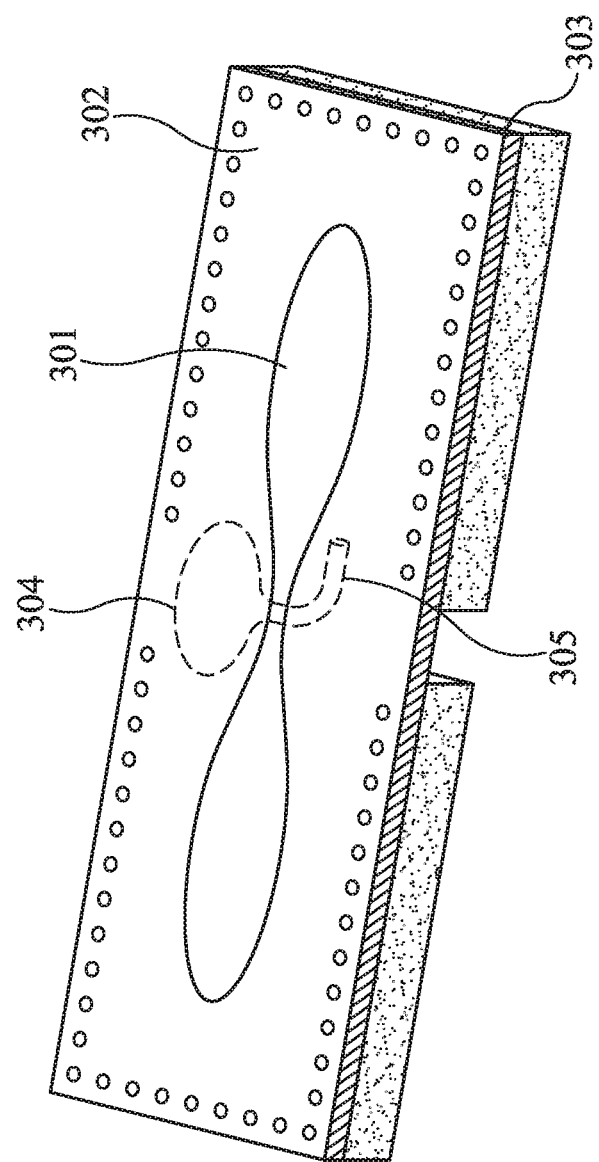
FIG. 3 is a perspective view of an antenna structure and an example of an antenna feeding structure for feeding energy into the antenna structure. This feeding structure is useful with embodiments of the antenna structures disclosed herein.

FIG. 3 shows an antenna structure and an antenna feeding structure. In some instances, the antenna may be fed by a microstrip line 305 printed on the inner surface of the flexible PCB material 303. That inner surface is the surface of the flexible material 303 that is opposite the surface metallization 302. Microstrip line 305 is terminated by elliptic shaped capacitive disk 304. Capacitive disk 304 may have a variety of shapes. Preferably the shape and location of the capacitive disk provides for a relatively short microstrip line. In other embodiments, the capacitive coupling can be replaced with an ohmic connection, implemented by a conductive via.

In addition, an RF sensor may include a detector diode. The detector diode may be located on an a relatively rigid portion, or PCB antenna half, half thereby minimizing the electrical distance between the diode detector and the antenna.

Figure 4:
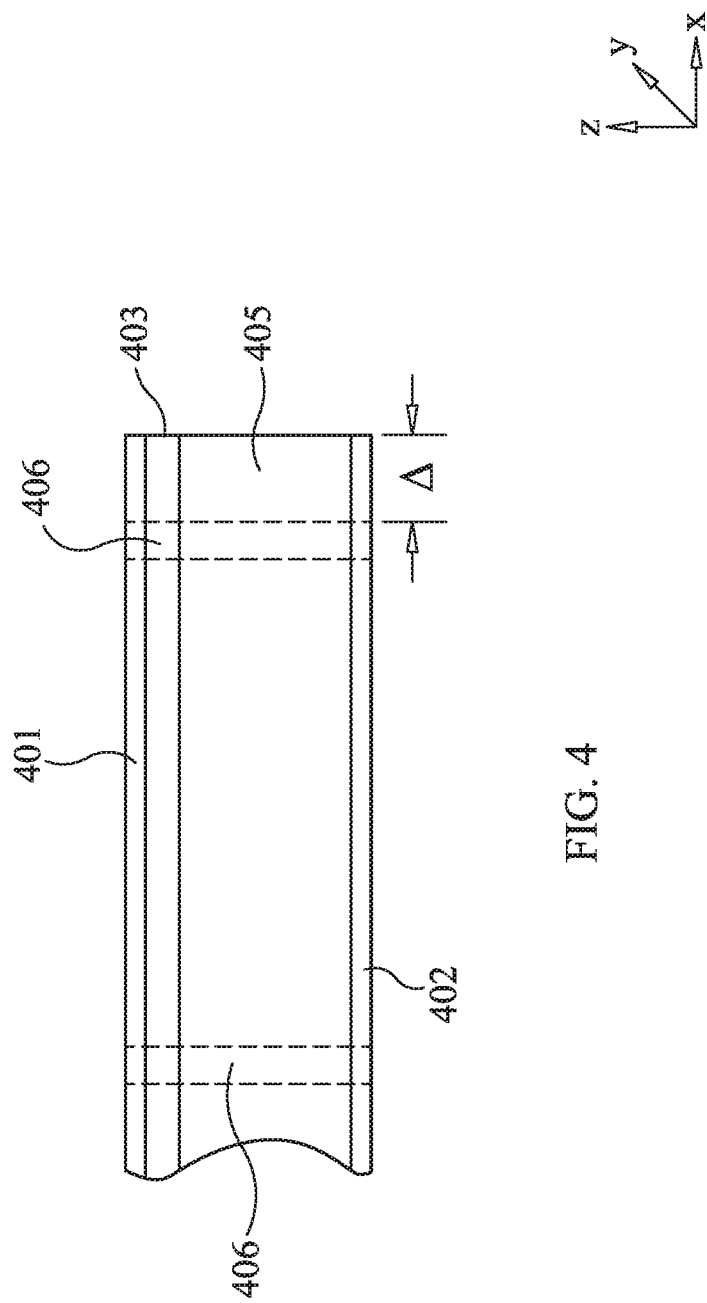
FIG. 4 is a cross section in the x-z plane of layers of antenna structures disclosed herein, and an x-y-z coordinate system for orientation.

FIG. 4 shows a cross section of the layers of the antenna embodiments disclosed herein. FIG. 4 shows top slotted metal layer 401; backplane metal layer 402; flexible dielectric layer 403; PCB dielectric layer 405; and conducting vias 406. In some embodiments, top slotted metal layer 401 and backplane metal layer 402 are interconnected with conducting vias 406. The conductive layers are supported by dielectric layers. Flexible layer 403 (for example comprising Mylar), and PCB dielectric layer 405 (for example FR-4 material) support the conductive layers. The conductive layers 401 and 402 protrude in the plane of the layers beyond the shorting vias 406 by a shorting distance Δ. The existence of this shorting distance Δ allows for the creation of a short circuited plate transmission line. This short circuited plate transmission disrupts the flow path of the surface current on the top surface 401 from closing its current path on the outside skin of the ground plane 402. This limits radiation of electrical field in the negative Z direction, and also reduces reverse radiation intensity.

Those of ordinary skill in the art will readily envision a variety of other structures for performing the function and obtaining the results and advantages described herein. Each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and that configurations will depend upon the specific application or applications for which the inventive teachings are used. Those skilled in the art will recognize, or be able to ascertain using no more than routine experimentation, many equivalents to the specific inventive embodiments described herein. The foregoing embodiments are presented by way of example only and that, within the scope of the appended claims and equivalents thereto, inventive embodiments may be practiced otherwise than as specifically described and claimed.

The antenna structures of the invention are preferably formed by conventional PCB manufacturing techniques known to those skilled in the art. U.S. Pat. No. 5,499,444 for example discloses methods for manufacturing a rigid flexible PCB.

The antenna structures of the invention are preferably incorporated into a wearable, such as a wrist strap shirt or trousers so that when the wearable is worn on a body, the antenna structures are each substantially flush with a surface of the body of the wearer. For example, the antenna structure may be molded into a band designed to be secured around the wrist, ankle, neck, or chest. For example, antenna structures of the invention may be sown into a pocket, or secured by sowing, into a region of fabric of a shirt or trousers. In addition, the method of fabrication of the antenna structures also includes electrically connecting the antenna structure to a source of electrical power, or including a source of electric power in the antenna structure. In addition, the method of fabrication comprises coupling the signal feed and a detector to suitable electronics for using the antenna to radiate signal towards the body of the human or other animal and analyzing the signal received by the antenna structure to determine physiologically relevant information therefrom. In a preferred embodiment, some part of this suitable electronics my reside on one or both faces of the intermediate section 512 of FIG. 5, as well as on any one or more of the backsides of sections 510, 511, 513, and 514.

In use, the antenna structure radiates broadband energy toward a body part, and received reflected energy from that body part. The radiated energy and reflected energy are analyzed by electronics implementing models of physiological activity, for example models of heart rate, artery diameter, and blood flow, to provide an estimate or measure of the physiological quantity modeled.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The invention claimed is:

1. A system for biometric sensing comprising a conformal flexible antenna structure, said conformal flexible antenna structure comprising:
   a first metal layer
   a flexible dielectric layer below the first metal layer;
   a first rigid dielectric segment below the flexible dielectric layer;
   a second rigid dielectric segment below the flexible dielectric layer;
   an antenna feed;
   wherein the first metal layer has a an upper major surface and a lower major surface;
   wherein the flexible dielectric layer has an upper major surface and a lower major surface;
   wherein the lower major surface of the first metal layer opposes regions of the upper major surface of the flexible dielectric layer;
   wherein the first rigid dielectric segment has an upper surface;
   wherein the second rigid dielectric segment has an upper surface;

wherein the upper surface of the first rigid dielectric segment opposes a first portion of the lower major surface of the flexible dielectric layer;

wherein the upper surface of the second rigid dielectric segment opposes a second portion of the lower major surface of the flexible dielectric layer;

wherein the first rigid dielectric segment and the second rigid section are spaced apart by a groove distance so that groove exists between the first rigid dielectric segment and the second rigid section such that the region of the conformal flexible antenna between the first rigid dielectric segment and the second rigid section is relatively flexible compared to flexibilities of the first rigid section and the second rigid section;

wherein the first metal layer has interior edges defining a slot through the first metal layer upper major surface and the first metal layer lower major surface;

wherein a first region of the slot is above a portion of the first rigid dielectric segment and another region of the slot is above a portion of the second rigid dielectric segment.

2. The system of claim 1, further comprising:
at least one backplane metal layer on backsides of one or more of the the rigid dielectric segments so as to cause radiation emitted by the antenna to become unidirectional.

3. The system of claim 2, further comprising:
conducting vias configured to connect the first metal layer and the backplane metal layer, said conducting vias disposed at least a shorting distance away from edges of both the first metal layer and the backplane metal layer, said shorting distance configured to allow creation of a short circuited plate transmission line.

4. The system of claim 1, wherein said system is designed to function within in the frequency range from 3.1 GHz to 10.6 GHz.

5. The system of claim 1, wherein a shape of the slot is configured to cause the antenna to be well matched in a bandwidth of at least 5 GHz in an ultra wide band of 3.1 GHz to 10.6 GHz.

6. The system of claim 1, wherein a shape of the slot is configured to allow heart rate detection by the antenna to be tolerant to misplacement up to about 6 mm in the plane parallel to the skin surface, from a point directly above any artery in a wrist area.

7. The system of claim 1, wherein the shape of the slot follows a substantially exponential taper terminated at a substantially circular termination, said circular termination having a diameter larger than width of an end of the exponential taper.

8. The system of claim 1, wherein at least one of the flexible dielectric layer and the plurality of rigid dielectric segments are realized on printed circuit board.

9. The system of claim 1, wherein the rigid dielectric segments are adhered to the flexible dielectric layer one or more spacing distances away from each other, and wherein said spacing distances are configured to provide flexible interconnections to the rigid dielectric segments.

10. The system of claim 9, wherein the spacing distances are sized to limit total amount of radiation emitted into the public under limits set by regulatory agencies.

11. The system of claim 1, wherein the antenna feed is terminated by a capacitive disk substantially in the shape of an ellipse.

12. A conformal antenna structure, comprising:
a relatively flexible dielectric layer having a lower surface opposing an upper surface;
a first relatively rigid dielectric layer having a lower surface and an upper surface;
a second relatively rigid dielectric layer having a lower surface and an upper surface;
a first region of said relatively flexible dielectric layer extending over the upper surface of said first relatively rigid section;
a second region of said relatively flexible dielectric layer extending over the upper surface of said first relatively rigid section;
said first region of said relatively flexible dielectric layer bonded or cobonded to said upper surface of said first relatively rigid section;
said second region of said relatively flexible dielectric layer bonded or cobonded to said upper surface of said second relatively rigid section;
a first metallic layer having a lower surface and an upper surface;
the lower surface of said first metallic layer bonded or cobonded to a region of the upper surface of said relatively flexible section;
wherein the lower surface and the upper surface of said first metallic layer defines a slot extending through said first metallic layer;
wherein a portion of said slot extends over said the upper surface of said first relatively rigid dielectric layer; and
wherein a portion of said slot extends over said the upper surface of said second relatively rigid dielectric layer.

13. The structure of claim 12 wherein a third region of said relatively flexible dielectric layer extends between said first region of said relatively flexible dielectric and said second region of said relatively flexible dielectric layer.

14. The structure of claim 12 further comprising:
a first metal layer on the lower surface of said first relatively rigid dielectric layer;
and a second metal layer on the lower surface of said second relatively rigid dielectric layer;
wherein the first metal layer and the second metal layer function as a ground plane.

15. The structure of claim 12 further comprising:
a third relatively rigid dielectric layer having a lower surface and an upper surface;
a fourth relatively rigid dielectric layer having a lower surface and an upper surface;
wherein regions of said relatively flexible dielectric layer extends over the upper surfaces of said third relatively rigid section and said fourth relatively rigid section.

16. The structure of claim 12 wherein said relatively flexible dielectric layer comprises a third region extending between said first region of said relatively flexible dielectric layer and said second region of said relatively flexible dielectric layer; and
wherein the third region or said relatively flexible dielectric layer does not extend over any portion of either said first relatively rigid dielectric layer or said second relatively rigid dielectric layer.

17. The structure of claim 12 in which said relatively flexible dielectric layer is flexed so that said first relatively rigid dielectric layer and said second relatively rigid dielectric layer are not coplanar.

18. The structure of claim 12 designed so that the antenna is well matched in a bandwidth of at least 5 GHz in a UWB frequency range of 3.1 GHz to 10.6 GHz.

19. The structure of claim 12 further comprising an antenna feed structure and a diode detector.

* * * * *